United States Patent [19]

Aslam et al.

[11] Patent Number: 5,726,295
[45] Date of Patent: Mar. 10, 1998

[54] PHOTOACTIVE COUMARIN DERIVATIVES

[75] Inventors: Mohammad Aslam; Michael T. Sheehan; Debasish Kuila, all of Corpus Christi, Tex.

[73] Assignee: Hoechst Celanese Corp., Somerville, N.J.

[21] Appl. No.: 813,097

[22] Filed: Mar. 7, 1997

[51] Int. Cl.$^6$ .................. C07D 311/20; C07D 335/06
[52] U.S. Cl. .................. 534/556; 534/557; 430/170; 430/192; 430/193
[58] Field of Search .................. 534/556, 557

[56] References Cited

U.S. PATENT DOCUMENTS

| | | | |
|---|---|---|---|
| 2,859,112 | 11/1958 | Sus et al. | 534/556 X |
| 4,211,791 | 7/1980 | Buckle et al. | 424/304 |
| 4,339,552 | 7/1982 | Balanson et al. | 430/192 |
| 4,588,670 | 5/1986 | Kelly et al. | 430/165 |
| 4,853,315 | 8/1989 | McKean et al. | 430/192 |
| 4,942,225 | 7/1990 | Lorenz | 534/560 |
| 5,501,936 | 3/1996 | Hosoda et al. | 430/191 |
| 5,532,107 | 7/1996 | Oie et al. | 430/192 |
| 5,541,033 | 7/1996 | Blakeney et al. | 430/192 |

FOREIGN PATENT DOCUMENTS

| | | |
|---|---|---|
| 2-61640 | 3/1990 | Japan. |
| 3-79670 | 4/1991 | Japan. |

OTHER PUBLICATIONS

Buckle et al., J. Med. Chem., 26(2), 251–254, 1983.
Eistert et al., Chem. Ber., 109(10), 3462–3472, 1976.
Hinman et al., J. Am. Chem. Soc., 79, 3789–3800, 1957.
Jefferson et al., "Acid–catalyzed Hydrolysis of 4–Diazo–Isothiochroman–3–one. Comparison With the Acyclic Analog and the Corresponding Oxygen System", Can. J. Chem., 75, 56–59 (1997).
A. Hermodson, W.M. Barker, K.P. Link/Studies of the 4–Hydroxycoumarins. Synthesis of the Metagolites and Some Other Derivatives of Warfarin—Journal of Medicinal Chemistry, 1971, vol. 14, No. 2, pp. 167–169.
Chemical Abstracts, 113: 68407 (1990).
Chemical Abstracts, 115: 244059 (1991).

*Primary Examiner*—Fiona T. Powers
*Attorney, Agent, or Firm*—Balaram Gupta

[57] ABSTRACT

A new class of 3,4-dihydrocoumarin derivatives which are useful as photoactive compounds in a wide variety of applications including photoresists and other opto-electronic applications are disclosed and claimed. Preferred embodiments include ether, ester, carbonate, and sulfonate derivatives of 5-hydroxy, 6-hydroxy, and 7-hydroxy-3-diazo-4-oxo-3,4-dihydrocoumarins. These compounds exhibit very high photosensitivity in the deep ultraviolet (DUV) region (ca. 250 nm), and therefore, are useful as photoactive compounds in DUV photoresist formulations.

23 Claims, No Drawings

5,726,295

PHOTOACTIVE COUMARIN DERIVATIVES

BACKGROUND OF THE INVENTION

1. Field of the Invention

The present invention relates to novel, ethers, carboxylic acid and sulfonic acid esters, and carbonates of 3-diazo-2, 4-dioxo-benzo-heterocyclic compounds such as 3-diazo-3, 4-dihydrocoumarins, which are useful synthetic intermediates in a wide variety of applications including photoresists, opto-electronics, agricultural, and pharmaceutical applications. More specifically, the present invention relates to 6-(3-diazo-4-oxo-3,4-dihydrocoumarinyl) ethers, carboxylic acid and sulfonic acid esters, and carbonates, which are useful as photoactive compounds in the photoresist formulations having applications in the deep ultraviolet region.

2. Description of the Prior Art

It is well-known that diazo compounds are used as "photoactive-compounds" (PACs) in photoresist formulations. For example, diazonaphthoquinones (DNQs) are widely used as PACs in positive photoresist formulations. The DNQs, for example, contain a wide variety of ballast groups which can be tailored to adjust the solubility of DNQs before and after exposure to actinic radiation such as ultraviolet in the 360–450 nm region. The DNQs also undergo photochemical transformation when exposed to actinic radiation. Furthermore, when DNQs are blended with phenolic resins, they tend to promote the solubility of the phenolic resins after exposure to radiation. The unexposed DNQs having the ballast groups on the other hand inhibits dissolution of the phenolic resins. As a result, fine patterns (lines) can be formed using appropriate photomasks and actinic radiation sources, and such patterns are useful in semiconductor/microelectronics industry.

As mentioned above, the commercially used photoresists containing the DNQs are frequently used in the 360–450 nm region of the electromagnetic spectrum. However, the current trend in the electronic industry is to develop semiconductor devices having extremely fine patterns. In order to obtain such fine patterns there is a need to develop photoresist formulation that can be developed in the 240–260 nm (i.e., the deep ultraviolet, DUV, region).

However, the currently commercially used DNQs, after exposure to light, absorb strongly between 240–260 nm region, and therefore, preclude their use as PACs in the DUV photoresist formulations. Therefore, it is an object of this invention to provide novel PACs which have no or minimal absorptions in the DUV region and thus are useful in DUV photoresist formulations. It is also an objective of this invention to provide a cost-effective, economic process for the preparation of the novel PACs of this invention.

PRIOR ART

The following references are disclosed as background prior art.

U.S. Pat. No. 4,211,791 discloses novel substituted coumarins and indanediones and a process for preparing them.

U.S. Pat. No. 4,339,522 discloses an ultraviolet lithographic resist composition and a process of making such composition which contains phenolic-aldehyde resins sensitized with Meldrum's diazo or a homologue thereof.

U.S. Pat. No. 4,588,670 discloses a light sensitive triester of o-quinone diazide containing positive photoresist compositions.

U.S. Pat. No. 4,853,315 describes o-quinone diazide sulfonic acid monoesters useful as sensitizers for positive resists. The esters of 1-oxo-2-diazo-naphthalene sulfonic acid in which the sulfonic acid group is either at 4- or the 5-position of a 3 (or 4)-hydroxymethyl-tricyclo[5.2.1.0.$^{2,6}$] decane are useful as sensitizers for positive resists, particularly at 365 nm.

U.S. Pat. No. 4,942,225 describes preparation of diazo and azo compounds using azidoformamidium salts.

U.S. Pat. No. 5,501,936 discloses positive-working quinonediazide photoresist composition containing a cyclohexyl-substituted triphenylmethane compound which is capable of giving an extremely fine patterned resist layer.

U.S. Pat. No. 5,532,107 describes positive resist composition containing photosensitive agents, which are quinonediazide sulfonates of tris- or tetra-hydroxy derivatives of triphenyl alkanes.

U.S. Pat. No. 5,541,033 discloses o-quinonediazide sulfonic acid esters of phenolic compounds and their use in radiation-sensitive compositions.

Japanese Laid-open Pat. No. Heisei 2-61640 discloses photosensitive compositions comprising an alkali-soluble resin and a photosensitizer having a 2-diazo-1,3-diketo group. Specific photosensitizer compounds included mono-substituted 3-diazo-4-oxo-3,4-dihydrocoumarins (examples of substitutents included 7-methyl, 7-propyl, 7-methoxy, and 6-chloro). However, only the unsubstituted 3-diazo-4-oxo-3,4-dihydrocoumarin was used in the photoresist formulation.

Japanese Laid-open Pat. No. Heisei 3-79670 discloses a negative-type radiation sensitive resin composition containing radiation sensitive materials having a diazo keto group. Specific examples of radiation sensitive materials included substituted indanones, tetralones, tetrahydronaphthadiones, tetrahydroquinolones, and chromanones. Unsubstituted 3-diazo-4-oxo-3,4-dihydrocoumarin was also used as radiation sensitive material in this disclosure.

J. Med. Chem. 1971, Vol. 14, (pp. 167–168) describe the synthesis of 4,5-, 4,6-, or 4,7-dihydroxy coumarins.

All of the references described herein are incorporated herein by reference in their entirety.

SUMMARY OF THE INVENTION

Surprisingly, the present invention provides a novel class of compounds which can function effectively as PACs in the DUV region. The compounds of the present invention are ethers, carboxylic acid and sulfonic acid esters, and carbonates of 3-diazo-2,4-dioxo-benzo-heterocyclic compounds having the formula:

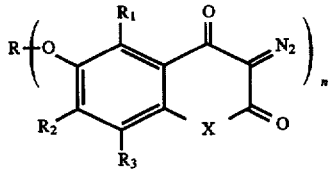

wherein:

(a) X is either oxygen or sulfur;

(b) R is selected from the group consisting of:
hydrogen,
alkyl of valence n having 1 to 16 carbon atoms,
aralkyl of valence n having 7 to 24 carbon atoms,
aryl of valence n having 6 to 24 carbon atoms,
acyl group having the formula, R'—(CO)$_n$—, where R' is an aliphatic or aromatic group of valence n having 1 to 24 carbon atoms, and n is an integer having a value of 1 to 10, alkoxy or aryloxy carbonyl having the formula, R'—(O—CO)$_n$—, where R' is an aliphatic or aromatic group of valence n having 1 to 24 carbon atoms, and sulfonylalkyl or sulfonylaryl having the formula, R'—(SO$_2$)$_n$—, where R' is an aliphatic or aromatic group of valence n having 1 to 24 carbon atoms;

(c) R$_1$, R$_2$, and R$_3$ are the same or different and are independently selected from the group consisting of:

hydrogen, fluorine, chlorine, bromine, or iodine, linear or branched alkyl and fluoroalkyl groups having the formula C$_q$H$_x$F$_y$, where q is an integer from 1 to 8, x and y are integers from 0 to 2q+1, and the sum of x and y is 2q+1;, aryl having 6 to 10 carbon atoms, aralkyl having 7 to 10 carbon atoms, alkoxy having 1 to 8 carbon atoms, aryloxy having 6 to 10 carbon atoms, and aralkyloxy having 7 to 10 carbon atoms; and (d) n is an integer having a value of 1 to 10.

In another aspect, this invention also provides a process for the preparation of the novel ethers, carboxylic acid and sulfonic acid esters, and carbonates of 5-, 6-, or 7-(3-diazo-2,4-dioxo-benzo-heterocyclic compounds) of the present invention. Thus, the process for preparing the novel ethers, carboxylic acid and sulfonic acid esters, and carbonates of 3-diazo-2,4-dioxo-benzo-heterocyclic compounds involves the steps of:

(a) subjecting a substituted hydroxy acetophenone to a substitution reaction in the presence of a suitable protecting group for a sufficient period of time and under suitable conditions of temperature and pressure to form the corresponding hydroxy-protected-acetophenone;

(b) subjecting said hydroxy-protected-acetophenone to suitable addition-cyclization conditions in the presence of a dialkyl carbonate and a catalyst for a sufficient period of time and under suitable conditions of temperature and pressure to form the corresponding benzo-heterocyclic compound containing a β-keto-enol group;

(c) subjecting said heterocyclic compound to suitable deprotection conditions for a sufficient period of time and under suitable conditions of temperature and pressure to form the corresponding hydroxy-benzo-heterocyclic compound containing a β-keto-enol group;

(d) subjecting said hydroxy-benzo-heterocyclic compound to suitable substitution conditions in the presence of a compound having the formula:

R—Z$_n$, where (i) Z is chlorine or bromine;

(ii) n is an integer having a value of 1 to 10; and (iii) R is selected from the group consisting of:

alkyl of valence n having 1 to 16 carbon atoms, aralkyl of valence n having 7 to 24 carbon atoms, aryl of valence n having 6 to 24 carbon atoms, acyl group having the formula, R'—(CO)$_n$—, where R' is an aliphatic or aromatic group of valence n having 1 to 24 carbon atoms, alkoxy or aryloxy carbonyl having the formula, R'—(O—CO)$_n$—, where R' is an aliphatic or aromatic group of valence n having 1 to 24 carbon atoms, and sulfonylalkyl or sulfonylaryl having the formula, R'—(SO$_2$)$_n$—, where R' is an aliphatic or aromatic group of valence n having 1 to 24 carbon atoms;

for a sufficient period of time and under suitable conditions of temperature and pressure to form the corresponding ether, carboxylic acid or sulfonic acid ester, or carbonate of benzo-heterocyclic compound containing a β-keto-enol group; and (e) subjecting said β-keto-enol compound from step (d) to suitable diazo transfer conditions in the presence of a diazo transfer agent for a sufficient period of time and under suitable conditions of temperature and pressure to form the corresponding ether, carboxylic acid or sulfonic acid ester, or carbonate of 3-diazo-2,4-dioxo-benzo-heterocyclic compound.

DETAILED DESCRIPTION OF THE INVENTION

Unexpectedly and surprisingly, it has now been found that ethers, carboxylic acid and sulfonic acid esters, and carbonates of 3-diazo-2,4-dioxo-benzo-heterocyclic compounds of the present invention exhibit low or no absorptions in the deep ultraviolet region (DUV), after exposure to DUV light. In addition, a wide variety of derivatives of these novel compounds can be readily made using a cost-effective, economic process as described herein. Thus, these compounds find utility as photoactive-compounds (PACs) in the DUV photoresist formulations.

The compounds of the present invention have the formula:

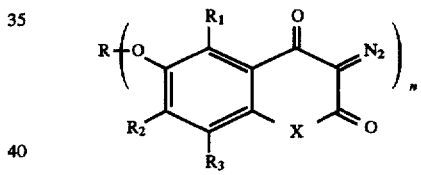

wherein:

(a) X is either oxygen or sulfur;

(b) R is selected from the group consisting of:

hydrogen, alkyl of valence n having 1 to 16 carbon atoms, aralkyl of valence n having 7 to 24 carbon atoms, aryl of valence n having 6 to 24 carbon atoms, acyl group having the formula, R'—(CO)$_n$—, where R' is an aliphatic or aromatic group of valence n having 1 to 24 carbon atoms, alkoxy or aryloxy carbonyl having the formula, R'—(O—CO)$_n$—, where R' is an aliphatic or aromatic group of valence n having 1 to 24 carbon atoms, and sulfonylalkyl or sulfonylaryl having the formula, R'—(SO$_2$)$_n$—, where R' is an aliphatic or aromatic group of valence n having 1 to 24 carbon atoms;

(c) R$_1$, R$_2$, and R$_3$ are the same or different and are independently selected from the group consisting of:

hydrogen, fluorine, chlorine, bromine, or iodine, linear or branched alkyl and fluoroalkyl groups having the formula C$_q$H$_x$F$_y$, where q is an integer from 1 to 8, x and y are integers from 0 to 2q+1, and the sum of x and y is 2q+1;

aryl having 6 to 10 carbon atoms,
aralkyl having 7 to 10 carbon atoms,
alkoxy having 1 to 8 carbon atoms,
aryloxy having 6 to 10 carbon atoms, and
aralkyloxy having 7 to 10 carbon atoms; and (d) n is an integer having a value of 1 to 10.

In the above definitions and throughout the present specification, alkyl means linear or branched alkyl having desirable number of carbon atoms and valence. Thus, a suitable R as specified herein may be a alkyl group of valence n having 1 to 16 carbon atoms, where n is an integer having a value of 1 to 10. The alkyl group is also often called as aliphatic group and may be acyclic (i.e., non-cyclic) or cyclic. Thus, suitable acyclic alkyl groups of valence 1 include methyl, ethyl, n- or iso-propyl, n-, iso-, or tert-butyl, linear or branched pentyl, hexyl, octyl, decyl, dodecyl, tetradecyl, and hexadecyl. The cyclic alkyl groups may be mono cyclic or polycyclic. Suitable example of mono-cyclic alkyl groups include substituted cyclopentyl, cyclohexyl, and cycloheptyl groups. The substituents may be any of the acyclic alkyl groups described herein.

Suitable bicyclic alkyl groups include substituted bicyclo [2.2.1]heptane, bicyclo[2.2.2]octane, bicyclo[3.2.1]octane, bicyclo[3.2.2]nonane, and bicyclo[3.3.2]decane, and the like. Examples of tricyclic alkyl groups include tricyclo $[5.4.0.0^{2,9}]$undecane, tricyclo$[4.2.1.2.^{7,9}]$undecane, tricyclo $[5.3.2.0.^{4,9}]$dodecane, and tricyclo$[5.2.1.0.^{2,6}]$decane. As mentioned herein the cyclic alkyl groups may have any of the acyclic alkyl groups as substituents.

The multivalent alkyl groups are derived from any of the alkyl groups mentioned hereinabove. Accordingly, a divalent acyclic group may be methylene, 1,1- or 1,2-ethylene, 1,1-, 1,2-, or 1,3 propylene and so on. Similarly, a divalent cyclic alkyl group may be 1,2- or 1,3-cyclopentylene, 1,2-, 1,3-, or 1,4-cyclohexylene, and the like. A divalent tricyclo alkyl groups may be any of the tricyclic alkyl groups mentioned herein above. A particularly useful tricyclic alkyl group in this invention is 4,8-bis(methylene)-tricyclo $[5.2.1.0.^{2,6}]$decane.

Suitable examples of monovalent aryl group having 6 to 24 carbon atoms include phenyl, tolyl, xylyl, naphthyl, biphenyls, bis-phenyls, tris-phenyls and the like. These aryl groups may further be substituted with any of the appropriate alkyl or aryl groups mentioned hereinabove. Similarly, appropriate polyvalent aryl groups as desired may be used in this invention. Representative examples of divalent aryl groups include phenylenes, xylylenes, naphthylenes, biphenylenes, and the like.

Representative examples of monovalent aralkyl having 7 to 24 carbon atoms include phenylmethyl, phenylethyl, diphenylmethyl, 1,1- or 1,2-diphenylethyl, 1,1-, 1,2-, 2,2-, or 1,3-diphenylpropyl, and the like. Appropriate combinations of substituted aralkyl groups as described herein having desirable valence may be used as a polyvalent aralkyl group.

Suitable alkyl, aryl or aralkyl substituents as $R_1$, $R_2$, and $R_3$ may be the same as described herein. Representative examples of linear or branched fluoroalkyl groups having 1 to 8 carbon atoms include, for example, trifluoromethyl, 1,1,2-trifluoroethyl, pentafluoroethyl, perfluoropropyl, perfluorobutyl, and 1,1,2,3,3-pentafluorobutyl.

As used herein, alkoxy means straight or branched chain alkoxy having 1 to 10 carbon atoms, and includes, for example, methoxy, ethoxy, n-propoxy, isopropoxy, n-butoxy, isobutoxy, tert-butoxy, pentyloxy, hexyloxy, heptyloxy, octyloxy, nonanyloxy, decanyloxy, 4-methylhexyloxy, 2-propylheptyloxy, and 2-ethyloctyloxy.

Examples of aryloxy having 6 to 10 carbon atoms may include phenoxy, tolyloxy, xylyloxy, and the like. Examples of aralkyloxy having 7 to 10 carbon atoms include phenylmethoxy, α- or β-phenethyloxy, 2-phenylpropyloxy, and the like.

Suitable examples of monovalent aliphatic acyclic acyl groups include acetyl, propionyl, n- or iso-butyryl, valeroyl, hexanoyl, octanoyl, dodecanoyl, strearyl, and the like. Examples of divalent aliphatic acyclic acyl groups include oxalyl, malonyl, succinoyl, glutaroyl, adipoyl, and the like. Suitable examples of aliphatic cyclic acyl groups include α-cyclopentylacetyl, α-cyclohexylacetyl, α-cycloheptylacetyl, β-cyclopentylpropionyl, and the like. Examples of divalent aliphatic cyclic acyl groups include 1,4-cyclohexane-dicarboxyl, 1,3-cyclohexane-dicarboxyl, and the like. Similarly, a wide variety of well known bicyclic and polycyclic acyl groups may be employed in this invention. A particularly useful tricyclic acyl group is 4,8-bis (carboxyl)tricyclo$[5.2.1.0^{2,6}]$decane.

The sulfonylalkyl or sulfonylaryl referred to herein may be derived from any of the alkyl, aryl, aralkyl groups described herein. As a representative example, without any limitation, methanesulfonyl, ethanesulfonyl, cyclohexanesulfonyl, benzenesulfonyl, p-toluenesulfonyl, and 4,4'-bis(sulfonylphenyl)ether may be enumerated.

Furthermore, and as used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

In another embodiment of this invention, the R group used to prepare the ether, carboxylic acid or sulfonic acid ester, or a carbonate of the present invention functions as a ballast group. As described herein, a ballast group is intended to mean a wide variety of alkyl, aryl, or aralkyl groups of desirable valence as described hereinabove. Any of the ballast groups well known in the art may be used. A number of different ballast groups are described in U.S. Pat. Nos. 4,588,670; 4,853,315; 5,501,936; and 5,532,107; all of which are incorporated herein by reference in their entirety.

It is believed that judicious selection of the ballast group is extremely critical to obtain desired intended benefit from the 3,4-dihydrocoumarin compound. The ballast group plays several roles particularly if it is used in the photoresist formulation. It is believed that the appropriate selection of ballast group can affect the solubility of the photoresist formulation formed therefrom. The ballast group further affects the shelf/formulation stability as well as the thermal stability of the photoresist formulation.

Particularly preferred compounds of this invention are those in which $R_1$ to $R_3$ are unsubstituted, i.e., in these compounds $R_1$ to $R_3$ are hydrogen. Also, the preferred compounds of this invention are 3,4-dihydrocoumarin derivatives, i.e., X is oxygen, and R is hydrogen. Specific examples of the preferred compounds of this type are as mentioned below:

3-diazo-4-oxo-5-hydroxy-3,4-dihydrocoumarin, Formula 1;

3-diazo-4-oxo-6-hydroxy-3,4-dihydrocoumarin, Formula 2; and 3-diazo-4-oxo-7-hydroxy-3,4-dihydrocoumarin, Formula 3.

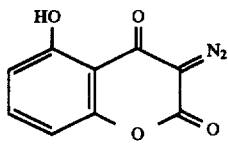
(1)

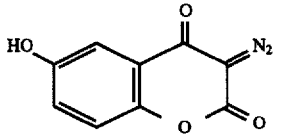
(2)

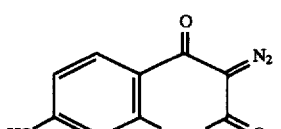
(3)

In another embodiment of this invention, the ether, carboxylic acid and sulfonic acid esters, and carbonates of substituted 3-diazo-4-oxo-3,4-dihydrocoumarin are the preferred compounds. Particulaly preferred compounds are unsubstituted, i.e., in which $R_1$ to $R_3$ are hydrogen.

Specific examples of ethers of 3-diazo-4-oxo-3,4-dihydrocoumarin are 3-diazo-4-oxo-6-benzyloxy-3,4-dihydrocoumarin (Formula 4); and 4,8-bis(3-diazo-4-oxo-6-oxymethyl-3,4-dihydrocoumarin) tricyclo[5.2.1.0.$^{2,6}$] decane (Formula 5) as shown below.

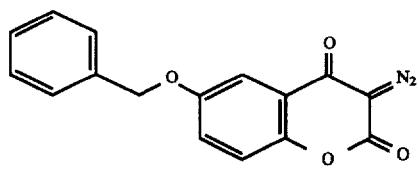
(4)

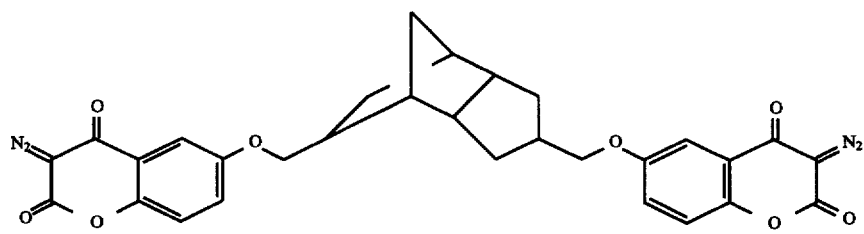
(5)

Specific examples of carboxylic acid esters of 3-diazo-4-oxo-3,4-dihydrocoumarin are as mentioned below:

4,8-bis(3-diazo-4-oxo-6-oxycarbonyl-3,4-dihydrocoumarin)tricyclo[5.2.1.0.$^{2,6}$]decane, Formula 6.

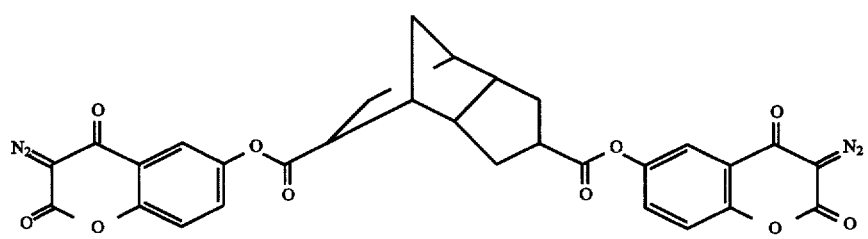
(6)

Specific examples of carbonate esters of 3-diazo-4-oxo-3,4-dihydrocoumarin are as mentioned below:

1',1',1'-tris-4-(3-diazo-4-oxo-3,4-dihydrocoumarin-6-carbonatophenyl)ethane, Formula 7;

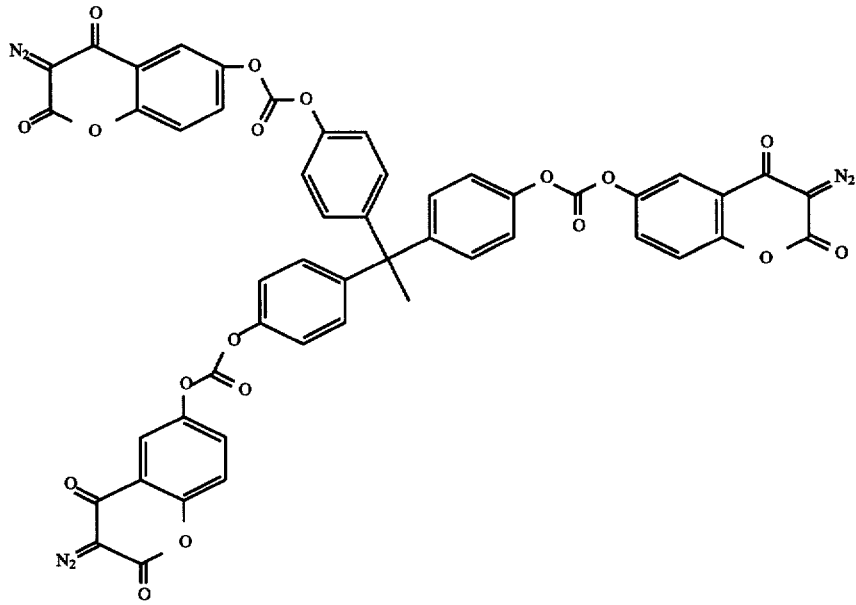

(7)

4,8-bis(3-diazo-4-oxo-3,4-dihydrocoumarin-6-formate) tricyclo[5.2.1.0.$^{2,6}$]decane, Formula 8,

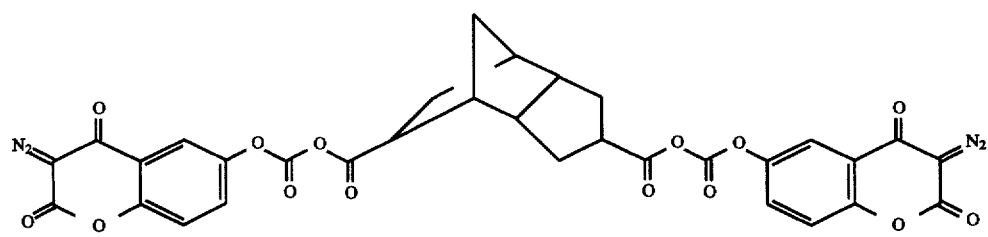

(8)

Specific examples of sulfonate esters of 3-diazo-4-oxo-3,4-dihydrocoumarin are as mentioned below:

4,4'-bis(3-diazo-4-oxo-6-oxysulfonylphenyl-3,4-dihydrocoumarin)ether, Formula 9

In another facet of this invention there is also provided a novel, unique, and efficient process for preparing the novel ethers, carboxylic acid and sulfonic acid esters, and carbonates of 3-diazo-2,4-dioxo-benzo-heterocyclic compounds comprising the steps of:

(a) subjecting a substituted hydroxy acetophenone to a substitution reaction in the presence of a suitable protecting group for a sufficient period of time and under

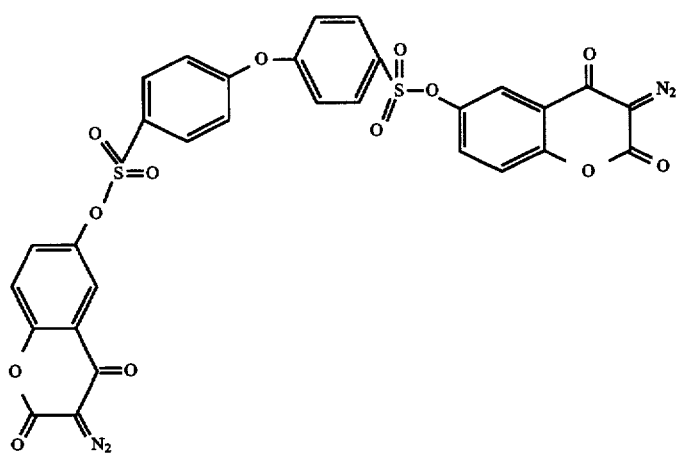

(9)

suitable conditions of temperature and pressure to form the corresponding hydroxy-protected-acetophenone;

(b) subjecting said hydroxy-protected-acetophenone to suitable condensation-cyclization conditions in the presence of a dialkyl carbonate and a catalyst for a sufficient period of time and under suitable conditions of temperature and pressure to form the corresponding benzo-heterocyclic compound containing a β-keto-enol group;

(c) subjecting said heterocyclic compound to suitable deprotection conditions for a sufficient period of time and under suitable conditions of temperature and pressure to form the corresponding hydroxy-benzo-heterocyclic compound containing a β-keto-enol group;

(d) subjecting said hydroxy-benzo-heterocyclic compound to suitable substitution conditions in the presence of a compound having the formula:

R—Z$_n$, where (i) Z is chlorine or bromine;

(ii) n is an integer having a value of 1 to 10; and (iii) R is selected from the group consisting of:

alkyl of valence n having 1 to 16 carbon atoms, aralkyl of valence n having 7 to 24 carbon atoms, aryl of valence n having 6 to 24 carbon atoms, acyl group having the formula, R'—(CO)$_n$—, where R' is an aliphatic or aromatic group of valence n having 1 to 24 carbon atoms, alkoxy or aryloxy carbonyl having the formula, R'—(O—CO)$_n$—, where R' is an aliphatic or aromatic group of valence n having 1 to 24 carbon atoms, and sulfonylalkyl or sulfonylaryl having the formula, R'—(SO$_2$)$_n$—, where R' is an aliphatic or aromatic group of valence n having 1 to 24 carbon atoms;

for a sufficient period of time and under suitable conditions of temperature and pressure to form the corresponding ether, carboxylic acid or sulfonic acid ester, or carbonate of benzo-heterocyclic compound containing a β-keto-enol group; and (e) subjecting said β-keto-enol compound from step (d) to suitable diazo transfer conditions in the presence of a diazo transfer agent for a sufficient period of time and under suitable conditions of temperature and pressure to form the corresponding ether, carboxylic acid or sulfonic acid ester, or carbonate of 3-diazo-2,4-dioxo-benzo-heterocyclic compound.

The starting material, i.e., the substituted hydroxy acetophenone has the formula, I as shown below:

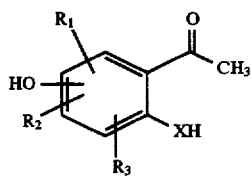

where R$_1$, R$_2$, R$_3$, and X are as defined above.

Utilizing the substituted hydroxy acetophenone (Formula I), it is believed that the process of the present invention proceeds as shown in Scheme I below:

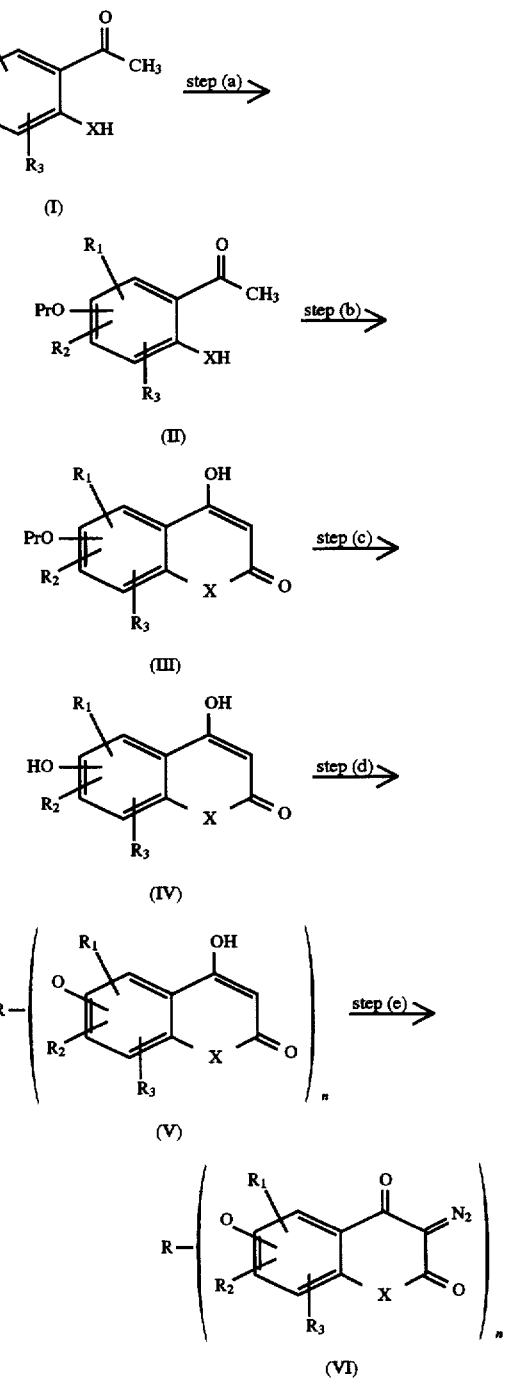

In Scheme I, steps (a) through (e) correspond to those steps (a) through (e) mentioned herein. In Scheme I, substituents R, R$_1$, R$_2$, R$_3$, X, and n are as defined above. The PrO— substituent in Formulae II and III is a protecting group for the phenolic hydroxy group as mentioned herein, which is described in more detail below.

In step (a), the phenolic hydroxy group in the substituted hydroxy acetophenone, Formula I is protected by a suitable protecting group using any of the well known methods in the art. A wide variety of protecting groups may be employed in step (a) provided that the protecting group is stable to the reactions conditions in step (b) of the process of the present invention. Suitable protecting groups for this purpose include, without limitation, benzyl, trimethylsilyl, tert-butyldimethylsilyl, 2-tetrahydropyranyl, and tert-butyloxycarbonyl. The benzyl group is particularly preferred protecting group.

The desired protecting group may be introduced into the Formula I in step (a) by any of the well known methods in the art. For instance, benzyl group may be introduced by reaction of the starting material, I with benzyl chloride (halide) under suitable substitution reaction conditions. The amount of benzyl chloride used in step (a) is generally stoichiometric, i.e., one mole of benzyl chloride per mole of the starting material, I. However, it is preferable that slight excess of benzyl chloride is employed in order to achieve complete conversion of starting material, I to the hydroxy-protected acetophenone, II.

In general, the substitution reaction in step (a) is carried out in the presence of a base, particularly when benzyl chloride (halide) is used in step (a). Any base may be used which will function for the substitution conditions to produce the desired end product, i.e., hydroxy-protected acetophenone, Formula II in step (a) of the process of the present invention. Accordingly, a suitable base includes an inorganic base such as a metal hydroxide, preferably an alkali metal hydroxide, an alkali metal carbonate, e.g., $K_2CO_3$; an alkali metal alkoxide (an ionic organic base), such as $NaOCH_3$, $KOC(CH_3)_3$, etc.; an alkali metal organic salt (an ionic organic base) such as potassium acetate, etc.; and an amine (a non-ionic organic base) such as pyridine, or a tri-lower-alkylamine, e.g., tripropylamine, trimethylamine, triethylamine, an hindered base such as 1,4-diazabicyclo[2.2.2]octane, and 4-dimethylaminopyridine, etc.

Additionally, suitable catalysts or co-catalysts may be used in step (a). Any material which accelerates or promotes the rate of substitution reaction when used in small quantities may be used as catalysts or co-catalysts in step (a). For example, when benzyl chloride is used in step (a), small amounts of potassium iodide substantially accelerates the rate of substitution to form the benzyl-protected hydroxy acetophenone.

The temperature at which step (a) is conducted ranges from about 50° C. to about 180° C., preferably from about 60° C. to about 100° C. The pressure in this step (a) is not critical and can be subatmospheric, atmospheric, or super atmospheric. The reaction times in step (a) will generally range from about 3 hours to about 12 hours or longer and sometimes under an inert atmosphere such as nitrogen or argon. Using the procedure of step (a) outlined herein, the substituted hydroxy acetophenone (Formula I, Scheme I) undergoes suitable substitution reaction to form the corresponding hydroxy protected acetophenone, Formula II, Scheme I.

In step (b), the hydroxy protected acetophenone, II is subjected to condensation-cyclization reaction to form the corresponding benzo-heterocyclic compound, Formula III, Scheme I. A description of such condensation-cyclization reaction for the preparation of hydroxy-coumarins may be found in U.S. Pat. No. 4,211,791 incorporated herein by reference in its entirety.

Illustratively, the hydroxy protected acetophenone, II is reacted with diethyl carbonate, preferably in the presence of a suitable base. It is preferable that a strong base is employed in step (b) in order to obtain higher yields of the heterocyclic product, Formula III, Scheme I. Accordingly, suitable base for this reaction include sodium amide, sodium hydride, or potassium hydride. The amount of base employed in step (b) is from about 0.5 to about 6 moles per mole of hydroxy protected acetophenone, II. The preferred amount is from about 1 mole to about 1.5 moles per mole of II.

The temperature at which step (b) is conducted ranges from about 80° C. to about 200° C., preferably from about 100° C. to about 150° C. The pressure in this step (a) is not critical and can be subatmospheric, atmospheric, or super atmospheric. The reaction times in step (a) will generally range from about 4 hours to about 12 hours or longer and sometimes under an inert atmosphere such as nitrogen or argon. Using the procedure of step (a) outlined herein, the hydroxy protected acetophenone (Formula II, Scheme I) undergoes suitable addition-cyclization reaction to form the corresponding heterocyclic compound, Formula III, Scheme I.

In step (c), the protecting group is deprotected under suitable deprotection conditions to form the corresponding hydroxy benzo-heterocyclic compound, Formula IV, Scheme I. The conditions employed for the deprotection depends upon the type of protecting group employed. For instance, silyl groups or tetrahydropyranyl groups as described herein may be deprotected using a variety of acidic reaction conditions well known in the art.

As mentioned herein, a particularly useful protecting group in this invention is benzyl group which can be deprotected by subjecting the compound, III to hydrogenation conditions. Any suitable hydrogenation conditions known in the art may be used. For example, in this instance it has been found that the compound, III undergoes hydrogenation readily under hydrogen pressure in the range of from about 75 psi to about 150 psi over palladium catalyst. Various other catalysts such as platinum and supported metal catalysts may also be used. A particularly suitable catalyst in step (c) is 5% palladium supported on carbon.

The temperature at which step (c) is conducted ranges from about 20° C. to about 80° C., preferably from about 40° C. to about 60° C. The pressure in this step (c) is critical and generally super atmospheric pressures of from about 75 psi to about 150 psi is preferred or in an inert atmosphere such as nitrogen. The reaction times in step (c) will generally range from about 1 hour to about 8 hours or longer usually in an hydrogen atmosphere as described herein. Using the procedure of step (c) outlined herein, the substituted hydroxy-protected heterocyclic compound (Formula III, Scheme I) undergoes suitable deprotection reaction to form the corresponding hydroxy heterocyclic compound, Formula IV, Scheme I.

In step (d), the compound, IV is subjected to suitable substitution reaction with a wide variety of R—$Z_n$ compounds as described hereinabove. As mentioned hereinabove, the "R" group serves as a ballast group and appropriate selection of "R" group is critical in order to obtain the maximum benefit of the compound VI particularly as a photoactive-compound.

Accordingly, depending upon the type of R—$Z_n$ employed ethers, carboxylic acid or sulfonic acid esters, or carbonates of heterocyclic compound (Formula V, Scheme I) may be prepared. Thus, for instance reaction of compound IV with an alkyl, aryl, aralkyl halide results in a ether, V; reaction of compound IV with an aliphatic or aromatic acyl halide of the formula, R'—(COZ)$_n$, results in an ester, V, where R' is as defined above; reaction of compound IV with a suitable haloformates of the formula, R'—(OCOZ)$_n$ results in a carbonate, V; and reaction of compound IV with a suitable alkyl or arylsufonylhalide of the formula, R'—(SO$_2$Z)$_n$ results in a sulfonate, V.

The amounts of R—$Z_n$ employed in step (d) depends upon the value of n. For instance, if n=1, then one mole of R—$Z_n$ per mole of compound is employed. It is preferable that to obtain higher yields of compound V, slight excess in the range of 10 to 20 mole percent excess of R—$Z_n$ is used. Similarly, if n>1, then the amount of compound IV used is n moles of compound IV per mole of R—$Z_n$. Sometimes it is advantageous to employ less than the desired amounts of compound IV to obtain a compound which is partially substituted, i.e., in compound V, all of the functional groups of R—$Z_n$ is not substituted with compound IV.

In general in step (d), a base is also used. Suitable base in step (d) is the same base as used in step (a) as described hereinabove. The organic bases such as triethyl amine or hindered amine bases described herein are particularly suitable bases in step (d).

The temperature at which step (d) is conducted ranges from about 10° C. to about 180° C., preferably from about 20° C. to about 40° C. The pressure in this step (d) is not critical and can be subatmospheric, atmospheric, or super atmospheric. The reaction times in step (d) will generally range from about 3 hours to about 12 hours or longer and sometimes under an inert atmosphere such as nitrogen or argon. Using the procedure of step (d) outlined herein, the substituted hydroxy-benzo-heterocyclic compound (Formula IV, Scheme I) undergoes suitable substitution reaction to form the corresponding ether, carboxylic acid or sulfonic acid ester, or carbonate of 3-diazo-2,4-dioxo-benzo-heterocyclic compound, Formula V, Scheme I.

In step (e) the compound, V is finally subjected to diazo transfer reaction to form the compound, VI, Scheme I. The diazo transfer reaction can be carried out using any of the well known methods in the art. For instance, a description of a diazo transfer reaction may be found in U.S. Pat. No. 4,942,225 and in Org. Syn. Collective Vol. 5, pp 179–183; both of which are incorporated herein by reference in their entirety. It has now been found that p-toluenesulfonyl (tosyl) azide works as effective diazo transfer agent to form the diazo compound VI as shown in Scheme I.

The amount of tosyl azide used in step (e) is generally stoichiometric amount, i.e., one mole of azide per mole of the compound, V. It is preferable that slight excess of tosyl azide is employed in order to achieve complete conversion of compound, V to the diazo compound VI. It is also preferable that the reaction is carried out in the presence of suitable base. Examples of such base include triethylamine, pyridine, imidazole, and the like.

The temperature at which step (e) is conducted ranges from about 10° C. to about 50° C., preferably from about 20° C. to about 40° C. The pressure in this step (e) is not critical and can be subatmospheric, atmospheric, or super atmospheric. The reaction times in step (e) will generally range from about ¼ hour to about 4 hours or longer and sometimes under an inert atmosphere such as nitrogen or argon. Using the procedure of step (e) outlined herein, the substituted benzo-heterocyclic β-keto-enol compound (Formula V, Scheme I) undergoes suitable diazo transfer reaction to form the corresponding 3-diazo-2,4-dioxo-benzo-heterocyclic compound, Formula VI, Scheme I.

In one of the preferred embodiments of the process of this invention the preferred compounds formed from the process of this invention are ethers, carboxylic acid or sulfonic acid esters, and carbonates of 3-diazo-4-oxo-3,4-dihydrocoumarins, i.e., X is oxygen in Formulae I through VI in Scheme I. Accordingly, the substituted dihydroxy acetophenones, I (where X=O) may be employed as the starting material In this preferred embodiment.

In another preferred embodiment a variation of the synthetic procedure as enumerated in Scheme I may be employed to prepare the compounds, VI. Accordingly, in this preferred embodiment, the process for preparing ethers, carboxylic acid and sulfonic acid esters, and carbonates of 3-diazo-4-oxo-3,4-dihydrocoumarins comprises the steps of:

(a) subjecting a substituted 2,4(5 or 6)-dihydroxy acetophenone to a substitution conditions in the presence of a compound having the formula:

R—$Z_m$ where (i) Z is chlorine or bromine;

(ii) n is an integer having a value of 1 to 10; and (iii) R is selected from the group consisting of:

alkyl of valence n having 1 to 12 carbon atoms, aralkyl of valence n having 7 to 14 carbon atoms, aryl of valence n having 6 to 14 carbon atoms, acyl group having the formula, R'—$(CO)_n$—, where R' is an aliphatic or aromatic group of valence n having 1 to 14 carbon atoms, alkoxy or aryloxy carbonyl having the formula, R'—(O—CO)$_n$—, where R' is an aliphatic or aromatic group of valence n having 1 to 14 carbon atoms, and sulfonylalkyl or sulfonylaryl having the formula, R'—$(SO_2)_n$—, where R' is an aliphatic or aromatic group of valence n having 1 to 14 carbon atoms;

for a sufficient period of time and under suitable conditions of temperature and pressure to form the corresponding ether, carboxylic acid or sulfonic acid ester, or carbonate of 2-hydroxyacetophenone;

(b) subjecting said substituted 2-hydroxyacetophenone from step (a) to suitable addition-cyclization conditions in the presence of a dialkyl carbonate and a catalyst for a sufficient period of time and under suitable conditions of temperature and pressure to form the corresponding 4-hydroxy coumarin; and (c) subjecting said 4-hydroxy coumarin to suitable diazo transfer conditions in the presence of a diazo transfer agent for a sufficient period of time and under suitable conditions of temperature and pressure to form the corresponding ether, carboxylic acid or sulfouic acid ester, or carbonate of 3-diazo-4-oxo-3,4-dihydrocoumarin.

In this preferred embodiment, utilizing the substituted 2,4 (5 or 6)-dihydroxy acetophenones (Formula VII, Scheme II) as the starting materials, it is believed that the process proceeds as shown in Scheme II below:

Scheme II

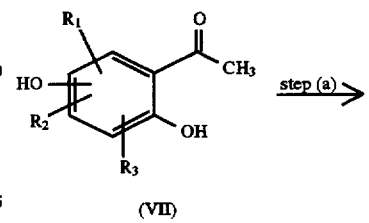

(VII)

Scheme II -continued

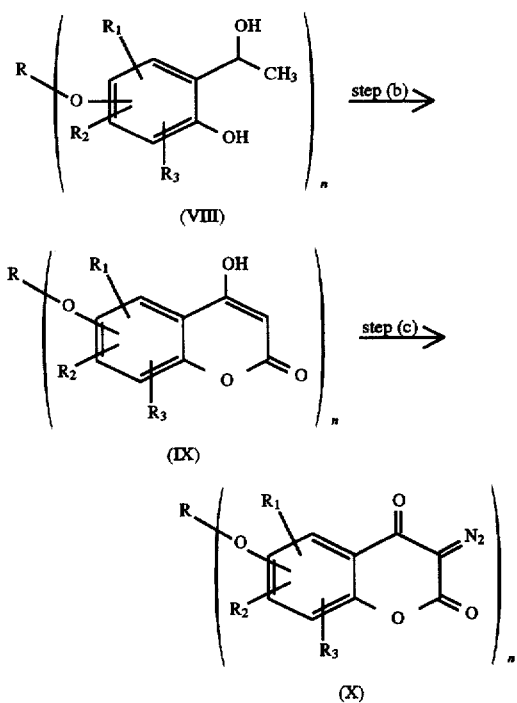

In Scheme II, steps (a) through (c) correspond to those steps (a) through (c) referred to in the preferred embodiment as mentioned herein. The step (a), Scheme II of this preferred embodiment may be carded out using the same procedures of step (d) of Scheme I as mentioned hereinabove. The step (b), Scheme II of this preferred embodiment may be carried out using the same procedures as described for step (b) of Scheme I. Finally, the step (c), Scheme II of this preferred embodiment may be carried out using the procedures described for step (e) of Scheme I.

This invention is further illustrated by the following examples which are provided for illustration purposes and in no way limit the scope of the present invention.

EXAMPLES (General)

In the Examples that follow, the following abbreviations are used:

- THPE—1',1',1'-Tris(4-hydroxyphenyl)ethane
- PDC—Pyridinium dichromate
- DHC—Dihydroxycoumarin
- THF—Tetrahydrofuran
- DMF—Dimethylformamide
- TLC—Thin layer chromatography
- HPLC—High performance liquid chromatography
- IR—Infrared spectroscopy
- NMR—Nuclear magnetic resonance spectroscopy, usually of either proton, $^1H$; and/or carbon 13, $^{13}C$ nuclei.
- DSC—Differential scanning calorimetry
- MS-APCI—Mass spectroscopy-Atmospheric pressure chemical ionization General Analytical Techniques Used for the Characterization: A variety of analytical techniques were used to characterize the 3,4-dihydrocoumarin compounds of the present invention which included the following:

IR: IR spectra of samples were taken using a Nicolet 20SXB FTIR Spectrometer.

NMR: $^1H$ and $^{13}C$ NMR spectra were recorded on a Bruker 400 MHz spectrometer with 5 mm probes at 400 and 100 MHz, respectively.

HPLC: Samples were analyzed with a Hewlett Packard 1090 Series II liquid chromatograph equipped with a 254 nm UV detector and a 150×4.6 mm column packed with 5μ Spherisorb C18. The injenction volume was 5 μL. Gradient elution at room temperature and at 1.1 ml/min was carded out with methanol and 0.1% aqueous acetic acid. The volume concentration of methanol in the eluent was increased from 20% to 90 over the first thirty minutes following injection and was then decreased back to 20% in the next five minutes.

DSC: A TA 3100 DSC was used to determine the $T_m$ of the dihydrocoumarin compounds of this invention. The heating rate was maintained at 10° C./minute, generally, over a temperature range of −25° C. to 300° C. The flow rate of nitrogen or air is maintained at 20 mL/min.

MS-APCI: A Finnigan SSQ-7000 mass spectrometer was used for all analyses. While electron ionization mass spectrometry in combination with Fourier Transform Infrared (FTIR) Spectroscopy is satisfactory for providing structural information about smaller size diazo compounds, as the size of diazo compounds increases, the analysis by electron ionization or desorption chemical ionization fails. Atmospheric pressure chemical ionization (APCI) LC/MS operated in the negative ion mode with a mobile phase containing 95% MeOH in water is found very useful to characterize large size diazo compounds although they react rapidly with methanol of the mobile phase.

EXAMPLE 1

Preparation of 4,8-bis(carboxy)tricyclo[5.2.1.0.$^{2,6}$]decane

A 500 mL round-bottom flask was charged with a solution of 4,8-bis(hydroxymethyl)tricyclo[5.2.1.0.$^{2,6}$]decane (10.1 g, 0.05 moles) in DMF (50 mL). To this solution was added slowly a solution of PDC (149 g, 0.4 moles) in DMF (200 mL). The mixture was then stirred at room temperature for about 40 hrs. The reaction was monitored by taking small aliquots of reaction mixture and analyzing by GC and TLC after work-up as follows. About 1 mL of reaction mixture was added to 7 mL of water and the precipitate formed was filtered and the filtrate was acidified with 1:1 HCl to a pH of 2, which was dissolved in ether for analysis. After complete conversion to diacid as evidenced by GC/TLC, the product was extracted with a large volume of diethyl ether and the ether layer was washed with water and dried over MgSO$_4$. The white solid acid was isolated using a rotary evaporator; yield, 5.2 g, (44%). The product was characterized by IR and NMR: IR (KBr) 3200–3600 cm$^{-1}$ (OH group), 1690 cm$^{-1}$ (C=O); $^{13}C$ NMR (DMSO-d$_6$): five observed peaks due to isomers at 179–180 ppm (C=O).

EXAMPLE 2

Preparation of 4,8-bis(chlorocarbonyl)tricyclo [5.2.1.0.$^{2,6}$]decane

The diacid prepared in accordance with Example 1 was converted to diacid chloride as follows. A 3-neck round-bottom flask equipped with a condenser and a stirrer was charged with of 4,8-bis(carboxy)tricyclo[5.2.1.0.$^{2,6}$]decane (2 g). Thionyl chloride (5.2 mL, 70 mmol) was added slowly at room temperature to under an atmosphere of $N_2$. After the addition was complete, the reaction mixture was heated to 85° C. in an oil bath and refluxed for 3 hours. Excess thionyl chloride was evaporated to obtain the desired acid chloride; yield 79%. The product was characterized by IR, MS, and NMR: IR (Film), 1780 & 1700 cm$^{-1}$ (C=O); APCI (-ve ion mode) flow injection (60:40 acetonitrile:$H_2O$ (HOAc) MS m/z calcd for $C_{12}H_{24}Cl_2O_2$ (M-H) 259, 261; $^{13}C$ NMR (CDCl$_3$) 175.7, 175.9, 176.1,176.3, 176.4 (C=O).

EXAMPLE 3

Preparation of 4,8-bis(chloromethyl)tricyclo [5.2.1.0.$^{2,6}$]decane

A 3-neck 100 mL round-bottom flask was charged with a solution of 4,8-bis(hydroxymethyl)tricyclo[5.2.1.0.$^{2,6}$] decane (10.2 g, 50 mmol) in DMF (10 mL) and pyridine (2 mL). To this solution was added thionyl chloride (14.6 mL, 0.2 moles) slowly using an addition funnel at 5° C. After the addition was complete, the flask was heated to reflux using an oil bath for 6 hrs (ca 160° C.). The reaction mixture was cooled, mixed with ice water (1:1), and the product was extracted with large amounts of ether. The ether layer was washed with saturated NaHCO$_3$ solution, water and dried over MgSO$_4$. The product was isolated by evaporation of ether; yield 50%. The product was characterized by NMR, GC, and GC/MS.

EXAMPLE 4

Preparation of 4-benzyloxy-2-hydroxy-acetophenone

A 500 mL 3-neck round-bottom flask equipped with a mechanical stirrer, condenser and a thermocouple was charged with acetone (150 mL), 2,4-dihydroxyacetophenone (15.2 g, 0.1 mol), benzyl chloride (16.5 g, 0.13 mol), potassium iodide (1.7 g, 0.01 mol) and potassium carbonate (15.2 g, 0.11 mol). The reaction mixture was heated to reflux for ~3 hrs under an atmosphere of $N_2$. The completion of the reaction was monitored by GC and HPLC. The mixture was filtered through a frit and the filtered cake (19.8 g) was washed with 150 mL of acetone. The filtrate was evaporated to dryness. The orange solid was recrystallized from methanol; yield 78.5%.

EXAMPLE 5

Preparation of 7-Benzyloxy-4-hydroxy-coumarin

4-Benzyloxy-2-hydroxy-acetophenone (20 g, 0.0825 mol), prepared in accordance with Example 4, was dissolved in 150 mL of toluene. To this solution was added diethyl carbonate (25.3 g, 0.21 mol) and the entire contents taken in a beaker was heated while stirring to dissolve the starting material. This solution was then taken in an addition funnel and was added at a rate of 7–8 mL/min (addition time=1.5 hrs) to a suspension of sodium hydride (4.3 g, 10.1 mol) in toluene (100 mL) taken in a 500 mL 4-neck flask equipped with a mechanical stirrer, a distillation apparatus (double jacketed-splitter heads) with a condenser, a thermocouple, and a thermometer to read the temperature of the distillate under $N_2$ atmosphere. The reaction flask was heated to 110°–115° C. with a heating mantle during the addition. Ethanol produced during this reaction is removed as an azeotrope with toluene. Additional toluene was added through the addition funnel to have enough of toluene in the reaction flask. The reaction mixture was refluxed for ~5 hrs to complete the reaction. The contents of the reaction flask were transferred to a separatory funnel and 400 mL of distilled water was added to separate into two phases. The aqueous layer was acidified to pH 2.0 with 1:1 dil. HCl and filtered under vacuum. The crude product was recrystallized from hot methanol; yield 84%.

EXAMPLE 6

Preparation of 4,7-Dihydroxy-coumarin

A 300 cc autoclave was charged with 7-benzyloxy-4-hydroxycoumarin (3 g, 3.7 mmol), prepared in accordance with Example 5, 5% Pd on carbon (0.18 g) and 85 mL of methanol and the autoclave was purged with $N_2$. The autoclave was pressurized with $H_2$ to a pressure of about 100 psi and maintained at that pressure. The exothermic reaction was carried out at ~50° C. for ~2 hrs. After the completion of hydrogenolysis, the reactor was flushed with $N_2$ and the contents were transferred into a beaker using a long pipet. The mixture containing Pd/C was dried over MgSO$_4$ and filtered through a frit. The filtrate was evaporated to dryness and finally dried overnight at 45° C. The purity of the material as determined by LC was 95%; yield ~90%. The product was characterized by NMR.

EXAMPLES 7–8

Example 4 was substantially repeated in Examples 7–8 with the exception that the materials and the amounts used were as set forth below:

| Materials | Amounts | |
|---|---|---|
| | Example 7 | Example 8 |
| 2,5-Dihydroxyacetophenone | 15.2 g(0.1 mol) | — |
| 2,6-Dihydroxyacetophenone | — | 15.2 g(0.1 mol) |
| Benzyl chloride | 16.5 g(0.13 mol) | 16.5 g(0.13 mol) |
| Potassium iodide | 1.66 g(0.01 mol) | 1.66 g(0.01 mol) |
| Potassium carbonate | 15.2 g(0.11 mol) | 15.2 g(0.11 mol) |
| The product formed and its yield were as follows: | | |
| 5-Benzyloxy-2-hydroxy-acetophenone | 22.0 g(91%) | — |
| 6-Benzyloxy-2-hydroxy-acetophenone | — | 10.5 g(43.5%) |

EXAMPLES 9–10

Example 5 was substantially repeated in Examples 9–10 with the exception that the materials and the amounts used were as set forth below:

| Materials | Amounts | |
|---|---|---|
| | Example 9 | Example 10 |
| 5-Benzyloxy-2-hydroxy-acetophenone (from Example 7) | 60.0 g(0.25 mol) | — |
| 6-Benzyloxy-2-hydroxy-acetophenone (from Example 8) | — | 19 g(0.0784 mol) |
| Diethyl carbonate | 75.9 g(0.63 mol) | 25.3 g(0.21 mol) |
| Sodium hydride | 12.84 g(0.32 mol) | 4.28 g(0.11 mol) |

-continued

| Materials | Amounts | |
|---|---|---|
| | Example 9 | Example 10 |
| The product formed and its yield were as follows: | | |
| 6-benzyloxy-4-hydroxy-coumarin | 47.6 g(71.6%) | — |
| 5-benzyloxy-4-hydroxy-coumarin | — | 7.64 g(36.3%) |

EXAMPLES 11–12

Example 6 was substantially repeated in Examples 11–12 with the exception that the solvent used was THF in Example 12 instead of methanol and the materials and the amounts used were as set forth below:

| Materials | Amounts | |
|---|---|---|
| | Example 11 | Example 12 |
| 6-benzyloxy-4-hydroxy-coumarin (from Example 9) | 11.9 g (0.044 mol) | — |
| 5-benzyloxy-4-hydroxy-coumarin (from Example 10) | — | 1 g (3.7 mmol) |
| 5% Pd on C | 0.7 g | 0.06 g |
| The product formed and its yield were as follows: | | |
| 4,6-Dihydroxy-coumarin | 5 g (65%) | — |
| 4,5-Dihydroxy-coumarin | — | 0.6 g (95%) |

EXAMPLE 13

Preparation of 4,8-bis(4-hydroxy-7-oxy-carbonyl-coumarin)tricyclo[5.2.1.0.$^{2,6}$]-decane A 50 mL 3 neck round-bottom flask equipped with a magnetic stirrer, a septum, an addition funnel and a $N_2$ outlet was charged with a solution of 4,7-dihydroxycoumarin prepared in accordance with Example 6 (1.0 g, 5.6 mmol) in THF (15 mL) and triethylamine (1.6 mL). To this solution was added dropwise a solution of 4,8-bis(chlorocarbonyl)-tricyclo[5.2.1.0.$^{2,6}$]decane prepared in accordance with Example 2 (0.75 g, 2.8 mmol) in dry THF (5 mL). The solution turned brown after addition of the acid chloride and the solution was stirred at room temperature for 24 hrs. The completion of the reaction was monitored by HPLC. Acetone (20 mL) was then added to this solution and the insoluble materials were filtered. The filtrate was rotavaporized to obtain a white solid; yield is quantitative. The product was characterized by NMR: $^{13}$C NMR (100 MHz in DMSO-$d_6$)): 173.9, 170.8, 163.5, 154.5, 152.6, 124.8, 118.0, 116.6, 109.3, 87.2. DSC, m.pt. 175° C.

EXAMPLE 14

Preparation of 4,8-bis(4-hydroxy-6-oxy-carbonylcoumarin)tricyclo[5.2.1.0.$^{2,6}$]decane Example 13 was substantially repeated in Example 14 with the exception of the materials and amounts used as set forth below:

| Materials | Amount |
|---|---|
| 4,6-dihydroxycoumarin (prepared in accordance with Example 11) | 5 g, 28 mmol |
| THF | 75 mL |
| Triethylamine | 8 mL |
| 4,8-bis(chlorocarbonyl)-tricyclo[5.2.1.0.$^{2,6}$]decane (prepared in accordance with Example 2) | 4.8 g, 18 mmol |
| THF | 25 mL |

The product was obtained in quantitative yields and characterized by NMR.

EXAMPLE 15

Preparation of 4,8-bis(4-hydroxy-5-oxy-carbonylcoumarin)tricyclo[5.2.1.0.$^{2,6}$]decane Example 13 was substantially repeated in Example 14 with the exception of the materials and amounts used as set forth below:

| Materials | Amount |
|---|---|
| 4,5-dihydroxycoumarin (prepared in accordance with Example 12) | 0.7 g, 3.6 mmol |
| THF | 15 mL |
| Triethylamine | 1.6 mL |
| 4,8-bis(chlorocarbonyl)-tricyclo[5.2.1.0.$^{2,6}$]decane (prepared in accordance with Example 2) | 0.5 g, 2 mmol |
| THF | 5 mL |

The product was obtained in quantitative yields and characterized by NMR and MS (APCI).

EXAMPLE 16

Preparation of 3-diazo-4-oxo-7-benzyloxy-3,4-dihydrocoumarin

A solution of 7-benzyloxy-4-hydroxy coumarin (2.5 g, 9.3 mmol; prepared in accordance with Example 5) in anhydrous THF (40 mL) was mixed with triethylamine (0.9 g, 9 mmol) taken in a 100 mL 3-neck round-bottom flask under an atmosphere of $N_2$. A solution of p-toluenesulfonyl azide (2.8 g, 14 mmol) in dry THF (20 mL) was added dropwise through an addition funnel. The mixture was stirred at room temperature for 3 hrs. The color of the solution turned orange. The solvent was rotary evaporated and the product was taken in $CH_2Cl_2$ and washed with water (3 times). Petroleum ether (twice the volume) was added to the solution and the solid precipitate was filtered with a flit and dried at 45° C. The product was recrystallized using $CH_2Cl_2$; yield 90%. The product was characterized by NMR: $^{13}$C NMR (100 MHz, $CD_2Cl_2$): 173.3, 165.4, 158.7, 156.0, 136.0, 129.1, 128.8, 128.0, 127.6, 113.9, 113.0, 103.0, 75.7, 71.2; DSC—m. pt. 191° C. followed by decomposition; IR (KBr): 2182, 2154, 1717, 1647, 1605 cm$^{-1}$; MS(APCI): (M+H), 295 (base peak).

EXAMPLE 17

Preparation of 3-diazo-4-oxo-5-benzyloxy-3,4-dihydrocoumarin

Example 16 was substantially repeated in Example 17 with the exception of the materials and amounts used as set forth below:

| Materials | Amount |
|---|---|
| 5-Benzyloxy-4-hydroxy-coumarin (prepared in accordance with Example 10) | 1 g, 3.7 mmol |
| THF | 20 mL |
| Triethylamine | 0.4 g, 3.7 mmol |
| p-toluenesulfonyl azide | 0.8 g, 4 mmol |
| THF | 5 mL |

After 3 hrs of reaction at room temperature, the solvent was evaporated and the product was placed in a freezer during which time the product crystallized. The crystals were removed using a frit; yield 56%. The product was characterized by NMR and IR: $^{13}$C NMR (100 MHz): 172.8, 159.1, 158.3, 156.0, 136.6, 136.3, 128.9, 128.3, 127.3, 110.5, 109.9, 109.6, 77.0, 71.3; IR(KBr): C=N$_2$ at 2124 cm$^{-1}$; C=O 1730 cm$^{-1}$; DSC—m. pt. 149° C. followed by a significant exothermic peak at ~200° C.; MS (APCI): +ve ion mode (energy induced dissociation)—M+H at 295, M+H—N$_2$ at 267; -ve ion mode, M$_2$-2N$_2$=532 (base peak).

EXAMPLE 18

Preparation of 4,8-bis(3-diazo-4-oxo-7-oxy-carbonyl-3,4-dihydrocoumarin)tricyclo[5.2.1.0.$^{2,6}$]-decane Example 16 was substantially repeated in Example 18 with the exception of the materials and amounts used as set forth below:

| Materials | Amount |
|---|---|
| 4,8-bis(4-hydroxy-7-oxy-carbonyl-3,4-dihydrocoumarin)-tricyclo[5.2.1.0.$^{2,6}$]-decane (from Example 13) | 0.5 g, 0.9 mmol |
| THF | 30 mL |
| Triethylamine | 0.3 mL, 2 mmol |
| p-Toluenesulfonyl azide | 0.4 g, 2 mmol |
| dry THF | 10 mL |

The product was characterized by NMR, IR, and MS: $^{13}$C NMR (100 MHz in DMSO-d$_6$): 173.4, 173.0, 157.7, 154.1, 129.2, 125.6, 119.3, 116.5, 111.4, 76.9; MS (APCI) -ve ion mode; M—2N$_2$+2 MeOH—H=603.2, M-N$_2$+MeOH—H= 599; FTIR (KBr): 2140 cm$^{-1}$ (C=N$_2$), 1732 cm$^{-1}$ (C=O).

EXAMPLE 19

Preparation of 4,8-bis -(3-diazo-4-oxo-5-oxy-carbonyl-3,4-dihydrocoumarin)tricyclo[5.2.1.0.$^{2,6}$]-decane Example 16 was substantially repeated in Example 18 with the exception of the materials and amounts used as set forth below:

| Materials | Amount |
|---|---|
| 4,8-bis(4-hydroxy-5-oxy-carbonyl-coumarin)-tricyclo[5.2.1.0.$^{2,6}$]-decane (from Example 15) | 1.1 g, 2 mmol |
| THF | 30 mL |
| Cesium carbonate | 1.3 g, 4 mmol |
| p-Toluenesulfonyl azide | 0.8 g, 4 mmol |
| dry THF | 10 mL |

The reaction mixture was filtered after stirring for about 10 hrs at room temperature, and the filtrate was chromatographed on silica gel using ethyl acetate/hexane solvent mixture. Polarity of the eluent was increased by adding methanol to ethyl acetate. The fractions were checked by TLC and characterized by HPLC, NMR, IR and MS: IR (KBr): 2154 cm$^{-1}$ (C=N$_2$), and 1732 cm$^{-1}$ (C=O); MS (APCI): M-N$_2$+MeOH—H=599.2; M-2N$_2$+2 MeOH—H= 603.2; $^{13}$C NMR: 77.6 (C=N$_2$).

EXAMPLE 20

Preparation of 4,8-bis(3-diazo-4-oxo-6-oxy-carbonyl-3,4-dihydrocoumarin)tricyclo[5.2.1.0.$^{2,6}$]-decane Example 16 was substantially repeated in Example 20 with the exception that the base used was cesium carbonate (4.2 g) and dry dichloromethane (95 mL) was used as the co-solvent. Various other materials and amounts used in Example 20 are as set forth below:

| Materials | Amount |
|---|---|
| 4,8-bis(4-hydroxy-6-oxy-carbonyl-coumarin)-tricyclo[5.2.1.0.$^{2,6}$]-decane (from Example 14) | 3.5 g, 6.4 mmol |
| CH$_2$CL$_2$ | 95 mL |
| Cesium Carbonate | 4.2 g, 13 mmol |
| p-Toluenesulfonyl azide | 2.5 g, 13 mmol |
| dry THF | 20 mL |

The product was characterized by LC.

EXAMPLE 21

Preparation of 1',1',1'-tris-(4-(4-hydroxy-7-coumarincarbanato)phenyl)ethane

This Example illustrates the preparation of carbonates of the photoactive compounds of the present invention. First the tris-chloroorthoformate of THPE was synthesized as follows. To a 100 mL 3-neck flask equipped with a 25 mL addition funnel, N$_2$ outlet and a septum was added solid triphosgene (1 g) inside a glove box. THF (3 mL) was added to the flask under N$_2$ through the septum to dissolve triphosgene and the flask was placed in an ice bath. Triethylamine (1.4 mL, 10 mmol) dissolved in THF (4 mL) was then added slowly to the flask through the septum. A white precipitate appeared. THPE (1.1 g, 3.8 mmol) dissolved in dry THF (7 mL) was added slowly to the flask through an addition funnel over a period of 45 minutes. The reaction was stirred at room temperature for 5 hrs and filtered using a frit and rinsed with THF and the filtrate was taken into an addition funnel under N$_2$ atmosphere.

A solution of 4,7-DHC (1 g, 5.6 mmol), prepared in accordance with Example 6, in THF (20 mL) was taken in another 100 mL 3-neck flask under N$_2$ atmosphere. To this solution was added triethylamine (1.7 mL). The THPE-tris-chloroorthoformate as prepared above was slowly added to 4,7-DHC solution at room temperature in about 14–16 hrs. The reaction mixture was then filtered through a frit and the residue was washed with 30 to 40 mL of HPLC grade acetone. The combined filtrates were evaporated to dryness; yield 1.6 g. The product was characterized by NMR.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound of the formula:

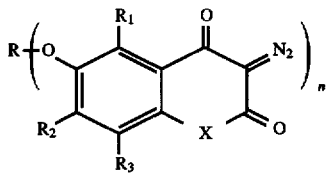

wherein:

(a) X is either oxygen or sulfur;
(b) R is selected from the group consisting of:
   aralkyl of valence n having 7 to 24 carbon atoms,
   aryl of valence n having 6 to 24 carbon atoms,
   acyl group having the formula, R'—(CO)$_n$—, where R' is an aliphatic or aromatic group of valence n having 1 to 24 carbon atoms,
   alkoxy or aryloxy carbonyl having the formula, R'—(O—CO)$_n$—, where R' is an aliphatic or aromatic group of valence n having 1 to 24 carbon atoms, and
   sulfonylalkyl or sulfonylaryl having the formula, R'—(SO$_2$)$_n$—, where R' is an aliphatic or aromatic group of valence n having 1 to 24 carbon atoms;
(c) $R_1$, $R_2$, and $R_3$ are the same or different and are independently selected from the group consisting of:
   hydrogen,
   fluorine, chlorine, bromine, or iodine,
   linear or branched alkyl and fluoroalkyl groups having the formula $C_qH_xF_y$, where q is an integer from 1 to 8, x and y are integers from 0 to 2q+1, and the sum of x and y is 2q+1;,
   aryl having 6 to 10 carbon atoms,
   aralkyl having 7 to 10 carbon atoms,
   alkoxy having 1 to 8 carbon atoms,
   aryloxy having 6 to 10 carbon atoms, and
   aralkyloxy having 7 to 10 carbon atoms; and
(d) n is an integer having a value of 1 to 10.

2. The compound as set forth in claim 1 wherein X is sulfur.

3. The compound as set forth in claim 1 wherein one of $R_1$ to $R_3$ is hydrogen.

4. The compound as set forth in claim 1 wherein two of $R_1$ to $R_3$ are hydrogen.

5. The compound as set forth in claim 1 wherein $R_1$ and $R_2$ are hydrogen, and $R_3$ is an alkyl having 6 to 8 carbon atoms.

6. A compound of the formula:

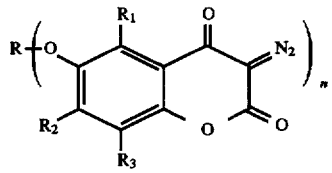

wherein:

(a) R is selected from the group consisting of:
   aralkyl of valence n having 7 to 24 carbon atoms,
   aryl of valence n having 6 to 24 carbon atoms,
   acyl group having the formula, R'—(CO)$_n$—, where R' is an aliphatic or aromatic group of valence n having 1 to 24 carbon atoms,
   alkoxy or aryloxy carbonyl having the formula, R'—(O—CO)$_n$—, where R' is an aliphatic or aromatic group of valence n having 1 to 24 carbon atoms, and
   sulfonylalkyl or sufonylaryl having the formula, R'—(SO$_2$)$_n$—, where R' is an aliphatic or aromatic group of valence n having 1 to 24 carbon atoms;
(b) $R_1$, $R_2$, and $R_3$ are the same or different and are independently selected from the group consisting of:
   hydrogen,
   fluorine, chlorine, bromine, or iodine,
   linear or branched alkyl and fluoroalkyl groups having the formula $C_qH_xF_y$, where q is an integer from 1 to 8, x and y are integers from 0 to 2q+1, and the sum of x and y is 2q+1;,
   aryl having 6 to 10 carbon atoms,
   aralkyl having 7 to 10 carbon atoms,
   alkoxy having 1 to 8 carbon atoms,
   aryloxy having 6 to 10 carbon atoms, and
   aralkyloxy having 7 to 10 carbon atoms; and
(c) n is an integer having a value of 1 to 6.

7. The compound as set forth in claim 6 wherein R is selected from the group consisting of:
   aralkyl of valence n having 7 to 24 carbon atoms, and
   aryl of valence n having 6 to 24 carbon atoms; where n is an integer having a value of 1 to 6.

8. The compound as set forth in claim 7 wherein one of $R_1$ to $R_3$ is hydrogen.

9. The compound as set forth in claim 7 wherein two of $R_1$ to $R_3$ are hydrogen.

10. The compound as set forth in claim 7 wherein $R_1$ to $R_3$ are hydrogen.

11. The compound as set forth in claim 10 wherein said compound is 3-diazo-4-oxo-6-benzyloxy-3,4-dihydrocoumarin having the formula:

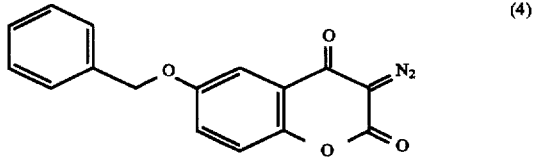

(4)

12. The compound as set forth in claim 6 wherein R is an acyl group having the formula, R'—(CO)$_n$—, where R' is an aliphatic or aromatic group of valence n having 1 to 24 carbon atoms, where n is an integer having a value of 1 to 4.

13. The compound as set forth in claim 12 wherein $R_1$ to $R_3$ are hydrogen.

14. The compound as set forth in claim 12 wherein said compound is 4,8-bis(3-diazo-4-oxo-6-oxycarbonyx-3,4-dihydrocoumarin)tricyclo[5.2.1.0.$^{2,6}$]decane having the formula:

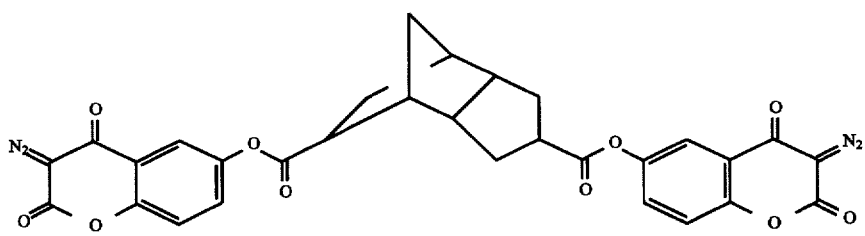

(6)

15. The compound as set forth in claim 6 wherein R is an alkoxy or aryloxy carbonyl having the formula, R'—(O—CO)$_n$—, where R' is an aliphatic or aromatic group of valence n having 1 to 24 carbon atoms, where n is an integer having a value of 1 to 4.

16. The compound as set forth in claim 15 wherein $R_1$ to $R_3$ are hydrogen.

17. The compounds as set forth in claim 16 wherein said compounds are, 1',1',1'-tris-4-(3-diazo-4-oxo-3,4-dihydrocoumarin-6-carbonatophenyl)ethane (Formula 7); and, 4,8-bis(3-diazo-4-oxo-3,4-dihydrocoumarin-6-formate) tricyclo[5.2.1.0.$^{2,6}$]decane (Formula 8):

18. The compound as set forth in claim 6 wherein R is a sulfonylalkyl or sulfonylaryl having the formula, R'—(SO$_2$)$_n$—, where R' is an aliphatic or aromatic group of valence n having 1 to 24 carbon atoms, where n is an integer having a value of 1 to 4.

19. The compound as set forth in claim 18 wherein $R_1$ to $R_3$ are hydrogen.

20. The compound as set forth in claim 19 wherein said compound is 4,4'-bis(3-diazo-4-oxo-6-oxysulfonylphenyl-3,4-dihydrocoumarin)ether having the Formula 9

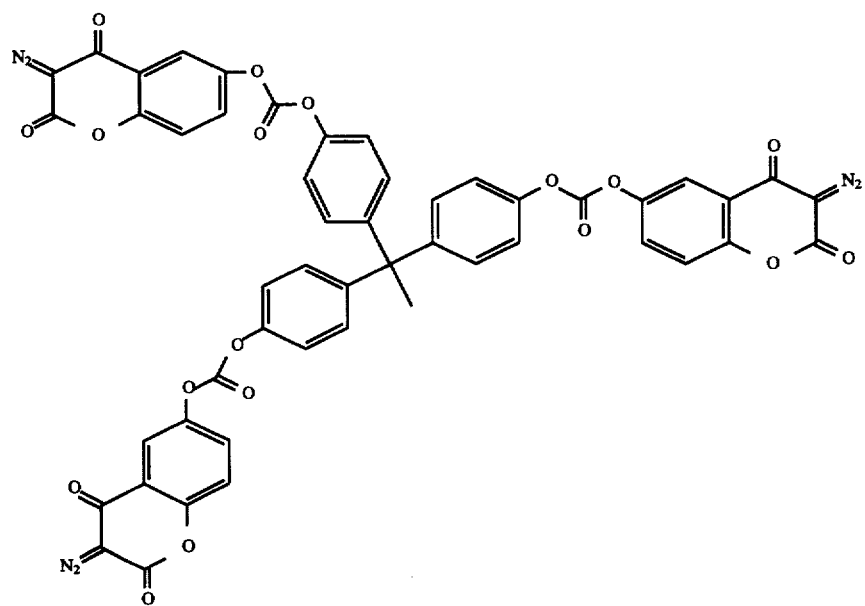

(7)

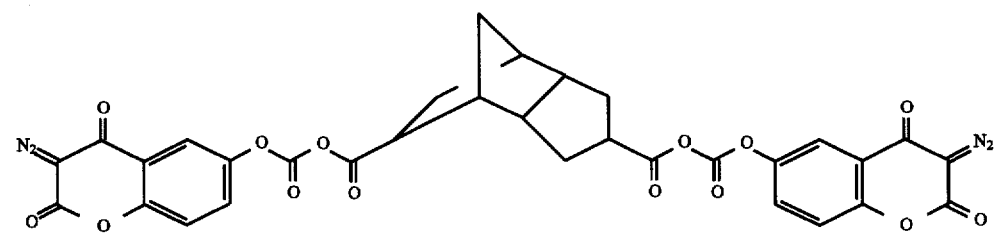

(8)

(9)

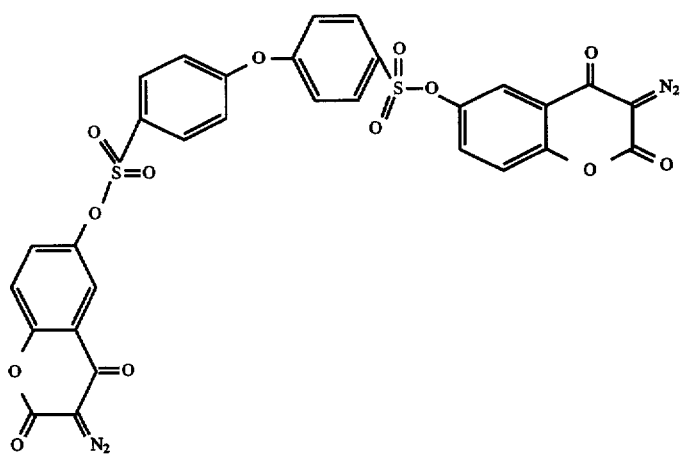

21. A compound of the formula:

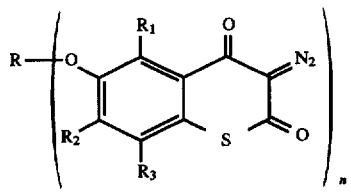

wherein:
(a) R is selected from the group consisting of:
   alkyl of valence n having 1 to 16 carbon atoms,
   aralkyl of valence n having 7 to 24 carbon atoms,
   aryl of valence n having 6 to 24 carbon atoms,
   acyl group having the formula, R'—(CO)$_n$—, where R' is an aliphatic or aromatic group of valence n having 1 to 24 carbon atoms,
   alkoxy or aryloxy carbonyl having the formula, R'—(O—CO)$_n$—, where R' is an aliphatic or aromatic group of valence n having 1 to 24 carbon atoms, and
   sulfonylalkyl or sufonylaryl having the formula, R'—(SO$_2$)$_n$—, where R' is an aliphatic or aromatic group of valence n having 1 to 24 carbon atoms;
(b) $R_1$, $R_2$, and $R_3$ are the same or different and are independently selected from the group consisting of:
   hydrogen,
   fluorine, chlorine, bromine, or iodine,
   linear or branched alkyl and fluoroalkyl groups having the formula
   $C_qH_xF_y$, where q is an integer from 1 to 8, x and y are integers from 0 to 2q+1, and the sum of x and y is 2q+1;,
   aryl having 6 to 10 carbon atoms,
   aralkyl having 7 to 10 carbon atoms,
   alkoxy having 1 to 8 carbon atoms,
   aryloxy having 6 to 10 carbon atoms, and
   aralkyloxy having 7 to 10 carbon atoms; and
(c) n is an integer having a value of 1 to 6.

22. The compound as set forth in claim 21 wherein $R_1$ to $R_3$ are hydrogen.

23. A compound of the formula:

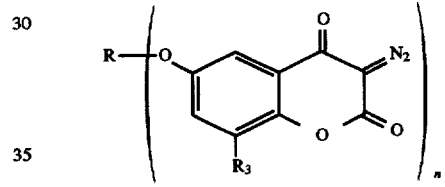

wherein:
(a) R is selected from the group consisting of:
   hydrogen,
   alkyl of valence n having 1 to 16 carbon atoms,
(b) $R_3$ is selected from the group consisting of:
   fluorine, chlorine, bromine, or iodine,
   linear or branched alkyl and fluoroalkyl groups having the formula $C_qH_xF_y$, where q is an integer from 6 to 8, x and y are integers from 0 to 2q+1, and the sum of x and y is 2q+1;,
   aryl having 6 to 10 carbon atoms,
   aralkyl having 7 to 10 carbon atoms,
   alkoxy having 4 to 8 carbon atoms,
   aryloxy having 6 to 10 carbon atoms, and
   aralkyloxy having 7 to 10 carbon atoms; and
(d) n is an integer having a value of 1 to 10.

* * * * *